United States Patent
Kwok et al.

(10) Patent No.: US 9,777,389 B2
(45) Date of Patent: Oct. 3, 2017

(54) FABRICATION OF NANOPORES USING HIGH ELECTRIC FIELDS

(71) Applicant: THE UNIVERSITY OF OTTAWA, Ottawa (CA)

(72) Inventors: Wing Hei Kwok, Ottawa (CA); Vincent Tabard-Cossa, Ottawa (CA); Kyle Alexander Zarkel Briggs, Ottawa (CA)

(73) Assignee: THE UNIVERSITY OF OTTAWA, Ottawa (CA)

( * ) Notice: Subject to any disclaimer, the term of this patent is extended or adjusted under 35 U.S.C. 154(b) by 368 days.

(21) Appl. No.: 14/399,071

(22) PCT Filed: May 7, 2013

(86) PCT No.: PCT/IB2013/000891
§ 371 (c)(1),
(2) Date: Nov. 5, 2014

(87) PCT Pub. No.: WO2013/167955
PCT Pub. Date: Nov. 14, 2013

(65) Prior Publication Data
US 2015/0108008 A1 Apr. 23, 2015

Related U.S. Application Data

(60) Provisional application No. 61/781,081, filed on Mar. 14, 2013, provisional application No. 61/643,651, filed on May 7, 2012.

(51) Int. Cl.
*C25F 3/14* (2006.01)
*B01D 67/00* (2006.01)
(Continued)

(52) U.S. Cl.
CPC ............ *C25F 3/14* (2013.01); *B01D 65/02* (2013.01); *B01D 67/009* (2013.01);
(Continued)

(58) Field of Classification Search
CPC ......................................... C25F 3/14
See application file for complete search history.

(56) References Cited

U.S. PATENT DOCUMENTS

2003/0010648 A1* 1/2003 Sun .................. B23H 3/00
205/640
2003/0080042 A1 5/2003 Barth et al.
(Continued)

FOREIGN PATENT DOCUMENTS

JP      20031462 A    1/2003
JP      2006523144 A    10/2006
(Continued)

OTHER PUBLICATIONS

Kwok, Harold, Briggs, Kyle and Tabard-Cossa, Vincent, "Rapid fabrication of sub 5 nm solid state nanopore for low cost biosensing", Abstract submitted for the Mar. 2013 meeting of the American Physical Society, Nov. 9, 2012.
(Continued)

*Primary Examiner* — Nicholas A Smith
(74) *Attorney, Agent, or Firm* — Harness, Dickey & Pierce, P.L.C.

(57) ABSTRACT

A method is provided for fabricating a nanopore in a membrane. The method includes: applying an electric potential across the membrane, where value of the electric potential is selected to induce an electric field which causes a leakage current across the membrane; monitoring current flow across the membrane while the electric potential is being applied; detecting an abrupt increase in the leakage current across the membrane; and removing the electric
(Continued)

potential across the membrane in response to detecting the abrupt increase in the leakage current.

18 Claims, 10 Drawing Sheets

(51) Int. Cl.
| | |
|---|---|
| *B01D 65/02* | (2006.01) |
| *G01N 33/487* | (2006.01) |
| *C25F 7/00* | (2006.01) |
| *G01B 7/00* | (2006.01) |
| *G01N 27/04* | (2006.01) |
| *G01N 33/00* | (2006.01) |
| *B81C 1/00* | (2006.01) |
| *B82Y 15/00* | (2011.01) |

(52) U.S. Cl.
CPC ............ *B81C 1/00087* (2013.01); *C25F 7/00* (2013.01); *G01B 7/00* (2013.01); *G01N 27/04* (2013.01); *G01N 33/00* (2013.01); *G01N 33/48721* (2013.01); *B01D 2321/22* (2013.01); *B01D 2323/42* (2013.01); *B01D 2325/02* (2013.01); *B81B 2203/0353* (2013.01); *B82Y 15/00* (2013.01); *G01N 2033/0095* (2013.01)

(56) References Cited

U.S. PATENT DOCUMENTS

| | | |
|---|---|---|
| 2005/0072689 A1 | 4/2005 | Spohr et al. |
| 2007/0172386 A1 | 7/2007 | Li et al. |
| 2009/0205960 A1 | 8/2009 | Schaffer et al. |
| 2010/0122907 A1 | 5/2010 | Stanford et al. |
| 2011/0174629 A1 | 7/2011 | Bouchet et al. |
| 2012/0103821 A1 | 5/2012 | Harrer et al. |
| 2014/0262820 A1 | 9/2014 | Kuan et al. |

FOREIGN PATENT DOCUMENTS

| | | |
|---|---|---|
| JP | 2007516792 A | 6/2007 |
| JP | 2009536107 A | 10/2009 |
| JP | 2013536089 A | 9/2013 |
| WO | WO-2008060324 A2 | 5/2008 |
| WO | WO-2011046706 A1 | 4/2011 |
| WO | WO-2011063458 A1 | 6/2011 |

OTHER PUBLICATIONS

International Search Report and Written Opinion of the International Searching Authority for PCT/IB2013/000891, mailed Aug. 28, 2013; ISA/CA.

International Search Report and Written Opinion of the International Searching Authority for PCT/162013/000884, mailed Sep. 5, 2013; ISA/CA.

M. Baklanov "Dielectric Films for Advanced Microelectronics", pp. 24-25 (2007).

J. Yota "Effects of Deposition Method of PECVD Silicon Nitride As MIM Capacitor Dielectric for GaAs HBT Technology", Sections of Experimental, and Results and Discussion; figure 8, Symposium on Silicon Nitride, (ECS) Meeting, (May 6, 2011).

Wu Meng-Yue et al., "Formation of nanopores in a SiN/SiO2 membrane with an electron beam", Applied Physics Letters, American Institute of Physics, vol. 87, No. 11 (2005).

\* cited by examiner

FABRICATION OF NANOPORES USING HIGH ELECTRIC FIELDS

CROSS-REFERENCE TO RELATED APPLICATIONS

This application claims the benefit of U.S. Provisional Application No. 61/643,651, filed on May 7, 2012 and U.S. Provisional Application No. 61/781,081, filed on Mar. 14, 2013. The entire disclosure of each of the above applications is incorporated herein by reference.

FIELD

The present disclosure relates to a technique for fabricating a nanopore using high electric fields.

BACKGROUND

Nanotechnology relies on our ability to manipulate matter and fabricate device structure at the nanometer scale. Present solid-state fabrication methods reproducibly achieving dimensional control at the nanometer scale are often complex and involve the use of expensive infrastructure, operated by highly qualified personnel. For instance, the problem of fabricating a molecular-scale hole, or nanopore, in a thin insulating solid-state membrane requires the use of focused high-energy particles, either produced by a dedicated ion beam machine (ion-beam sculpting) or a transmission electron microscope (TEM drilling). Although these advances in nanofabrication have placed the fabrication of nanoscale devices with sub-nm control within reach of the academic laboratories, they are poorly suited to mass-producing holes in a membrane to create nanopores. This represents a major barrier to the commercialization of any solid-state nanopore-based technologies for health science applications, including rapid DNA sequencing.

This section provides background information related to the present disclosure, which is not necessarily prior art.

SUMMARY

This section provides a general summary of the disclosure, and is not a comprehensive disclosure of its full scope or all of its features.

A method is provided for fabricating a nanopore in a dielectric membrane immersed in a solution containing ions. The method includes: applying an electric potential across the membrane, where value of the electric potential is selected to induce an electric field which causes a leakage current across the otherwise insulating membrane; monitoring current flow across the membrane while the electric potential is being applied; detecting a sudden irreversible increase in the leakage current across the membrane; and removing the electric potential across the membrane in response to detecting the sudden increase in the leakage current to stop the fabrication of the nanopore.

In one aspect, an abrupt increase in the leakage current is detected by comparing a value of the monitored current to a threshold and then ceasing to apply the electric potential when the value of the monitored current exceeds the threshold.

In another aspect, the membrane is disposed between two reservoirs filled with a fluid and thereby prevents the fluid from passing between the two reservoirs.

An apparatus is also provided for fabricating a nanopore in a membrane. The apparatus includes: two reservoirs fluidly coupled via a passageway to each other; a pair of electrodes electrically connected to a voltage source, such that one electrode is disposed in each of the two reservoirs and the pair of electrodes generate an electric potential across the membrane; a current sensor electrically coupled to one of the electrodes and operable to measure current flowing between the two reservoirs; and a controller interfaced with the current sensor, wherein the controller detects an abrupt increase in the measured current and, in response to detecting the abrupt increase in the measured current, removes the voltage across the electrodes.

Further areas of applicability will become apparent from the description provided herein. The description and specific examples in this summary are intended for purposes of illustration only and are not intended to limit the scope of the present disclosure.

DRAWINGS

Figure 1:
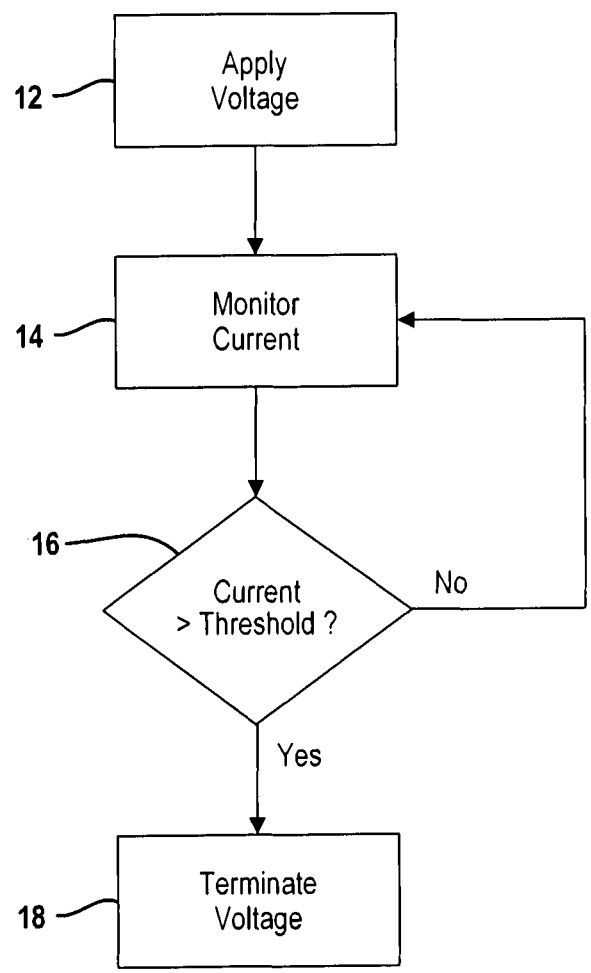
FIG. 1 is a flowchart depicting a method for fabricating a single nanopore in accordance with the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 depicts a simple and low-cost method for fabricating a single nanopore with sub-nm resolution (e.g., 1-100 nanometers) in a thin membrane. The method relies on applying a voltage across the thin membrane at 12 to generate a high enough electric field to induce a leakage current across the membrane. In some embodiments, the membrane is disposed between two reservoirs filled with a fluid, such that the membrane separates the two reservoirs and prevents flow of liquid between the two reservoirs. Current flow across the membrane is monitored at 14 while the electric field is being applied. The creation of a single nanopore (i.e., fluidic channel spanning the membrane) is indicated by an abrupt irreversible increase in the leakage current. To detect the creation of the nanopore, the monitored current can be compared at 16 to a pre-determined threshold. When the monitored current exceeds the threshold, the applied voltage is terminated at 18. Thus, the initial size of the nanopore can be set primarily based on the value of the current threshold although other factors influencing the size of the nanopore are further described below. While reference is made to formation of a nanopore, the techniques described herein are applicable more generally to holes of varying sizes.

Figure 2A:
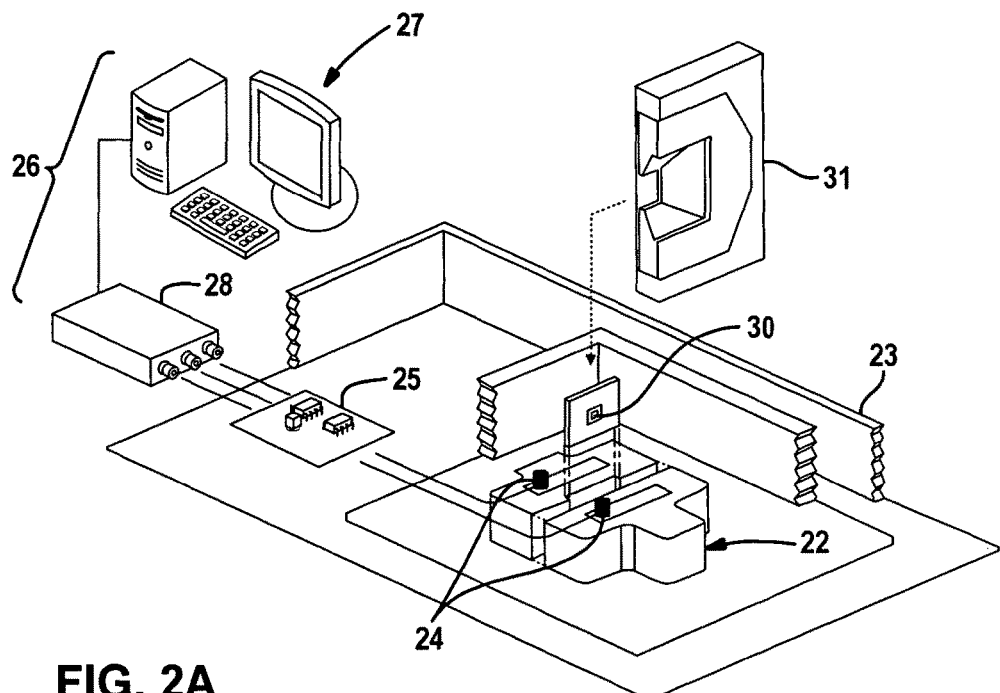
FIG. 2A is a diagram depicting an example setup for fabricating a nanopore.
Figure 2B:
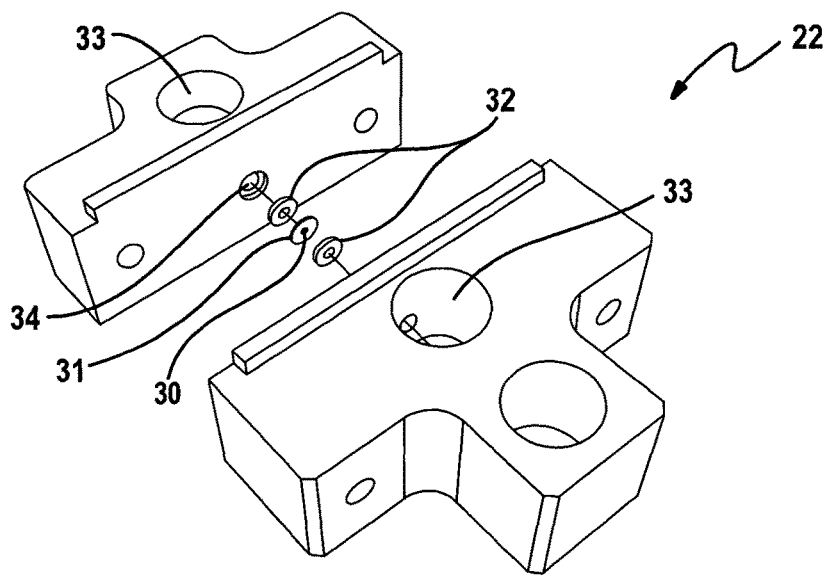
FIG. 2B is a diagram of an example fluidic cell.

Schematic of an example setup for fabricating a nanopore is shown in FIGS. 2A and 2B. The setup is comprised generally of a fluidic cell 22; a pair of electrodes 24 electrically coupled to a current amplifier circuit 25; and a controller 26 interfaced with the current amplifier circuit 25. The fluidic cell 22 is further defined by two reservoirs 33 fluidly coupled via a passageway 34 to each other as best seen in FIG. 2B. The current amplifier circuit 25 operates to create a potential between the electrodes and measure the current flow between the two reservoirs 33. In some embodiments, the controller 26 may be implemented by a data acquisition circuit 28 coupled to a personal computer 27 or another type of computing device. Thus, the setup is similar to what is commonly used for biomolecular detection in the nanopore sensing field. The fluidic cell 22 and/or the entire system can be disposed in a grounded faraday cage 23 to isolate electric noise. Other setups for fabricating a nanopore are contemplated by this disclosure.

In the example setup, a silicon chip 31 is used to house a membrane 30. The silicon chip 31 is sandwiched between two silicone gaskets 32 and then positioned between the two reservoirs 33 of the fluidic cell 22. In some embodiments, the fluidic cell 22 is comprised of polytetrafluoroethylene (PTFE) although other materials are contemplated. A small pressure is applied to the two gaskets 32 by the fluidic cell 22 to seal the contact tightly. The two reservoirs 33 are filled with a fluid containing ions, and the two electrodes 24 are inserted into the respective reservoirs of the fluidic cell 22. Example setups may include but are not limited to chloride-based salt solutions with Ag/AgCl electrodes or copper sulphate solutions with copper electrodes. The fluid could also be a non-aqueous solvent, such as 1M LiCl in ethanol. The fluid can be the same in both reservoirs and does not need to possess an active etching action against the membrane material. Other types of fluids and means of positioning the membrane between the two reservoirs are also envisioned, such as micro- and nanofluidics encapsulation.

In some embodiments, one of the electrodes may be placed in direct contact with surface of the membrane. In other embodiments, one of the electrodes may be a nano-electrode that is positioned to localize the electric field on the membrane and thereby localize the formation of the pore in the membrane. It is also understood that the more than two electrodes may be used. For example, one electrode may be placed into each reservoir with a third electrode placed into directed contact with the surface of the membrane. Other electrode arrangements are also contemplated by this disclosure.

In some implementations, the membrane 30 is comprised of a dielectric material such as silicon nitride ($SiN_x$). Membranes are preferably thin with a thickness of 10 nm or 30 nm although membranes having different thicknesses are contemplated by this disclosure. Membranes comprised of other dielectric materials, such as other oxides and nitrides, which are commonly used as gate materials for transistors, also fall within the scope of this disclosure. Likewise, atomically thin membranes may be comprised of other materials such as graphene, boron nitride and the like. It is also contemplated that the membranes may be comprised of multiple layers of materials, including dielectric materials and/or conductive materials.

Figure 3:
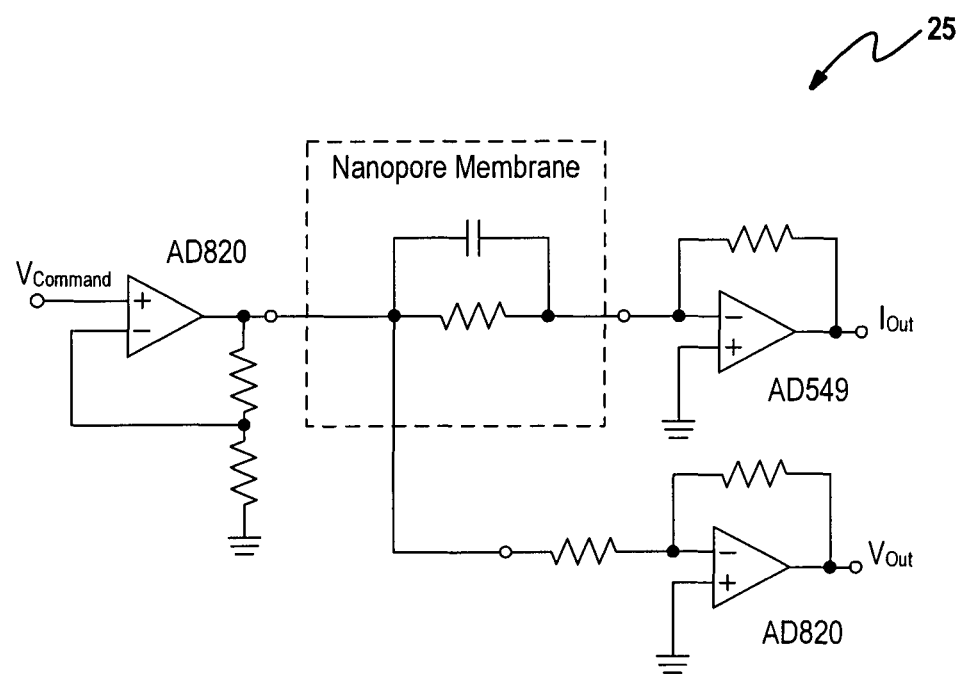
FIG. 3 is a schematic of an example current amplifier circuit which may be used to fabricate a nanopore.

In one example embodiment, the current amplifier circuit 25 relies on simple operation-amplifier circuit to read and control voltage and current as shown in FIG. 3. Op-amps are powered by a ±20 volt voltage source. In operation, the circuit takes in a command voltage ($V_{command}$) between ±10 volts from a computer controlled data acquisition card, which is amplified to ±20 volts, and sets the potential across the membrane. The applied potential ($V_{out}$) can also be measured by the current amplifier circuit 25. Current flow between the two electrodes is measured at one or both of the electrodes with pA sensitivity. More specifically, current is measured with a transimpedance amplifier topology. The measured current signal ($I_{out}$) is digitized by the data acquisition circuit and fed continuously into the controller. In this way, the current is monitored in real time by the controller, for example at a frequency of 10 Hz, though faster sampling rate can be used for faster response time, once the current reaches the threshold. Other circuit arrangements for applying a potential and measuring a current fall within the scope of this disclosure.

In the example embodiment, the current threshold is set to coincide with the sudden increase in current as to set the minimal size of the nanopore on the order of 1-nm. In other embodiments, the size of the nanopore can be set larger, however, by continuing to apply a potential across the membrane. That is, the size of the nanopore continues to increase as the monitored current continues to increase. Rather than setting the current threshold to coincide with the sudden increase in the leakage current, the value of the current threshold may be set to different values to achieve a nanopore of varying sizes. An exemplary technique for fine tuning the size of a nanopore is further described by Beamish et al in "Precise Control of the Size and Noise of Solid-state Nanopores using High Electric Field" Nanotechnology 23 405301 (2012) which is incorporated in its entirety herein by reference. Other techniques and arrangements for tuning nanopores are also contemplated by this disclosure.

In some embodiments, the electric potential is removed from the membrane before the abrupt increase in the leakage current (i.e., before pore formation). For example, the electric potential is removed after the monitored current exceeds a predefined threshold or after a specified amount of time but before the abrupt increase in leakage current. In this way, the pore may be partial drilled or formed in the membrane. The same or different process can then be used at a subsequent time to complete pore formation.

FIGS. 4A-4D further illustrate the technique for fabricating a nanopore in a membrane 41. For illustration purposes, the membrane 41 is comprised of silicon nitride having, for example a 10-nm or 30-nm thickness, t. More specifically, low-stress (<250 MPa) $SiN_x$ can be deposited on 200-μm thick silicon substrate 42 by low-pressure chemical vapour deposition (LPCVD). A 50 μm×50 μm window on the backside of a substrate is opened by KOH anisotropic chemical etching. The absence of pre-existing structural damage (e.g., pinholes, nono-crack, etc.) is inferred by the fact that no current (i.e., <10 pA) is measured across a membrane at low electric fields (e.g., <0.1 V/nm) prior to nanopore fabrication.

Figure 5:
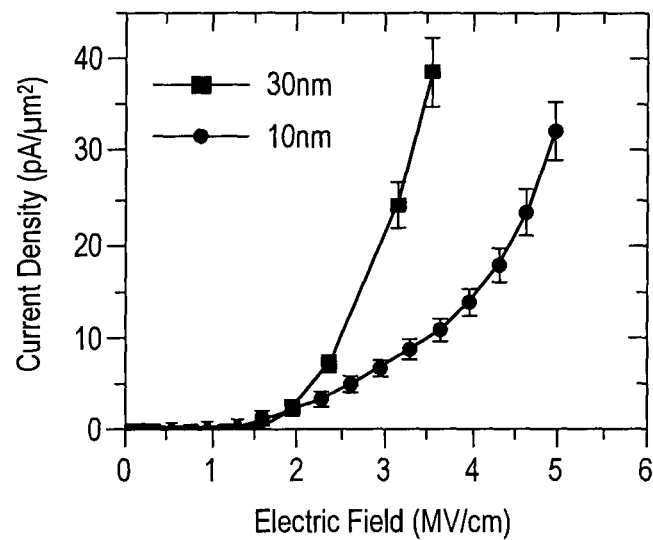
FIG. 5 is a graph depicting leakage current in the cell in relation to the applied electric field.

A single nanopore can be fabricated by applying a constant potential, ΔV, across a membrane 41. The value of the electric potential (e.g., 4 volts) is selected to induce an electric field which causes a leakage current across the membrane. In this example, the electric potential produces an electric field, E, on the order of 0.5 V/nm, in the membrane, where the electric field is defined as E=ΔV/t, and is approaching the dielectric breakdown strength of the material. For other situations, it is envisioned that the electric field will be greater than 0.1 V/nm and likely within the range of 0.2-1 V/nm. At these high field strengths, a sustainable leakage current, $I_{leakage}$, is observed through the membrane, which remains otherwise insulating at low fields. $I_{leakage}$ rapidly increases with electric field strength, but is typically in the range of tens of nanoamperes for the operating conditions as shown in FIG. 5. It is understood that the magnitude of the electric potential needed for pore creation may vary depending on the material of the membrane, thickness of the membrane as well as other factors.

Figure 4B:
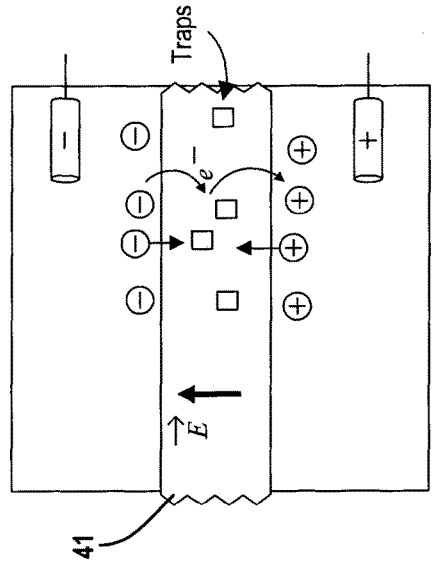
FIGS. 4A-4D are diagrams illustrating the fabrication of a nanopore in a thin membrane by high electric fields.

With reference to FIG. 4B, the dominant conduction mechanism in the dielectric membrane is attributed to a form of trap-assisted tunnelling of electrons supplied by ions in solution, since the membrane is too thick for significant direct quantum mechanical tunnelling and migration of impurities cannot produce lasting currents. Direct migration of electrolyte ions is also unlikely since for a given electric field strength, higher leakage currents are observed for thicker membranes. Free charges (electrons or holes) can be produced by redox reactions at the surface or by field ionization of incorporated ions. The number of available charged traps (structural defects) sets the magnitude of the observed leakage current. Accumulation of charge traps produced by electric field-induced bond breakage or energetic tunneling charge carriers leads to a highly localized conductive path and a discrete dielectric breakdown event as shown in FIG. 4C.

Figure 4D:
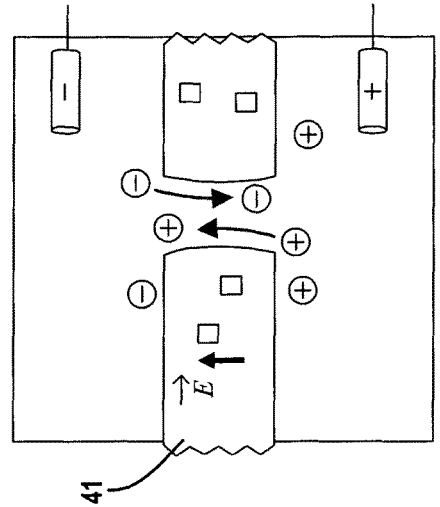
Figure 4A:
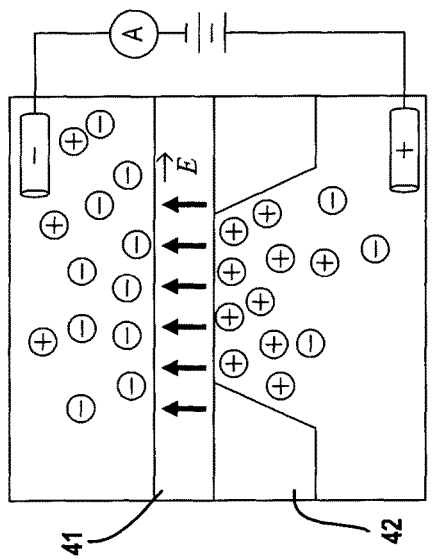
Figure 4C:
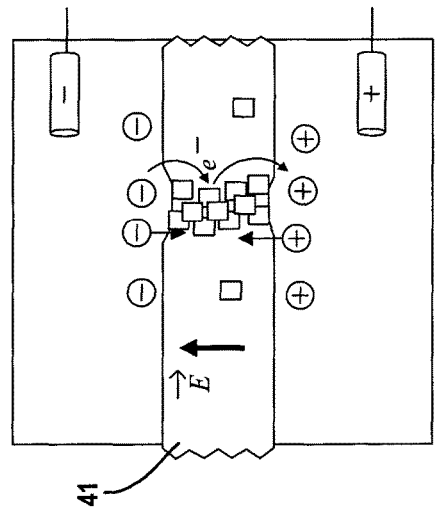

In FIG. 4D, a nanopore is formed by removal of membrane material at the leakage spot. The creation of a single nanopore (i.e. fluidic channel spanning the membrane) is indicated by a sudden irreversible increase in the leakage current, which is attributed to the onset of ionic current. A feedback control mechanism is used to rapidly terminate the applied potential when the current exceeds a pre-determined threshold, $I_{cutoff}$. In one example embodiment, the threshold may be a fixed value (e.g., 110 nA). In some embodiments, the threshold may vary, for example depending on the magnitude of the leakage current. For example, the threshold may be set to a multiplier (e.g., 1.5) of the leakage current before a pore is formed. In other embodiments, the threshold may be defined as a rate at which the monitored current is changing (e.g., ~10 nA/s for SiNx). It is readily understood that the value for the threshold may vary depending on the membrane material, membrane thickness as well as other factors.

Figure 6:
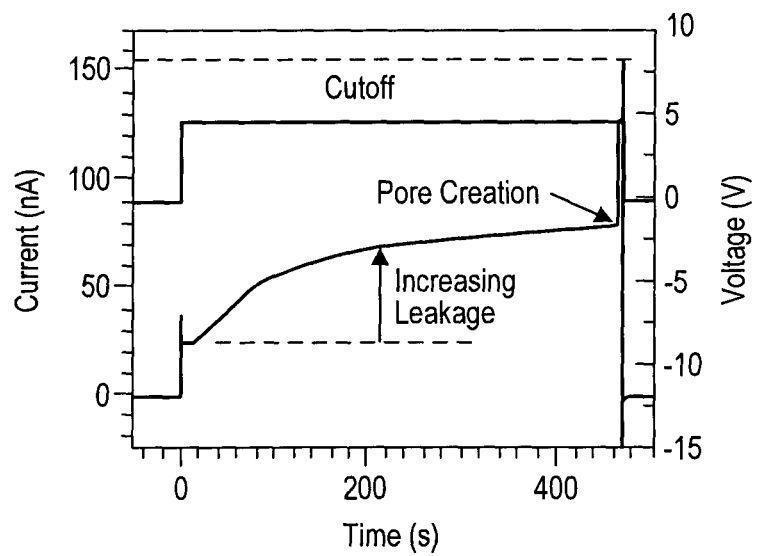
FIGS. 6 and 7 are graphs depicting a pore creation event in a membrane having a 10 nm and 30 nm thickness, respectively.
Figure 7:
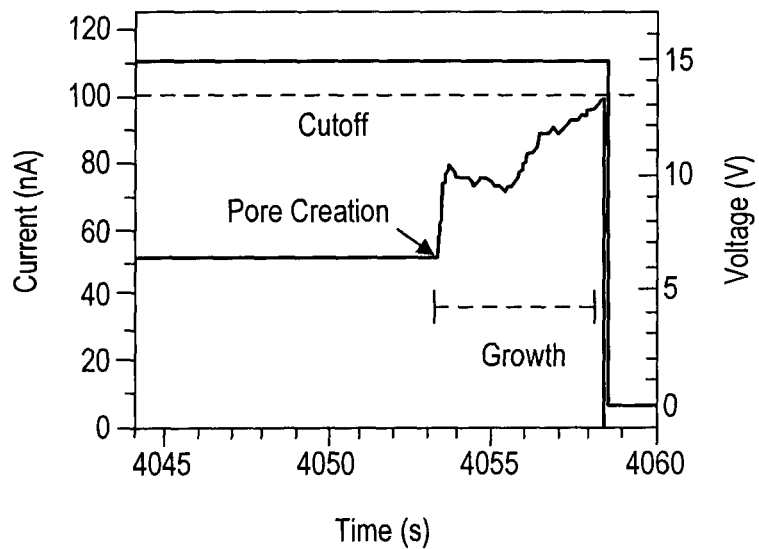

FIGS. 6 and 7 show such a pore creation event in a $SiN_x$ membrane having a 10 nm and 30 nm thickness, respectively. These results indicate that the value of $I_{cutoff}$ helps limit the initial size of the nanopore. A tight threshold can thus produce nanopores on the order of 2-nm in diameter or smaller. Following the nanopore fabrication event, the size of the nanpore can be enlarged with sub-nm precision by applying moderate AC electric field square pulses in the range of ±0.2-0.3 V/nm. This allows the nanopore size to be precisely tuned for a particular sensing application.

To infer the nanopore size upon fabrication, its ionic conductance, G, can be measured and related it to an effective diameter, d, assuming a cylindrical geometry and accounting for access resistance, using $$G = \sigma\left[\frac{4t}{\pi d^2} + \frac{1}{d}\right]^{-1},$$

where σ is the bulk conductivity of the solution. This method, practical for nanopores fabricated in liquids, provides a reasonable estimate of the pore size, which compares very well with actual dimensions obtained from transmission electron microscope (TEM) images, particularly for pores >5-nm.

Figure 8:
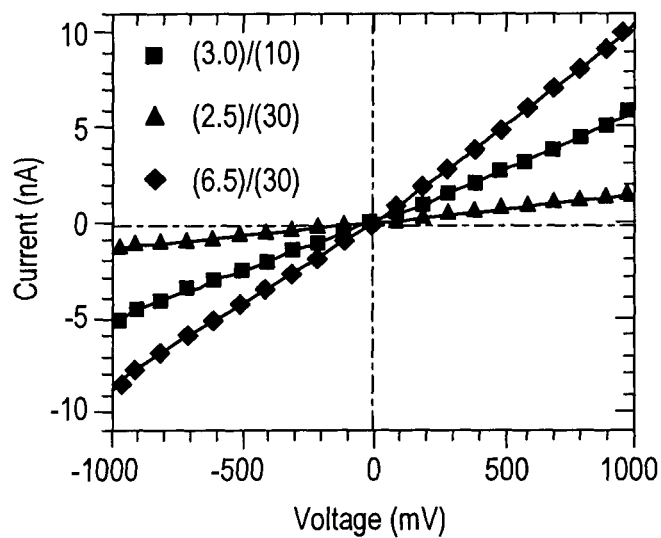
FIG. 8 is a graph depicting current-to-voltage curves for three independent nanopores fabricated on different membranes.

I-V curves are performed in a ±1 V window, where leakage current can safely be ignored. FIG. 8 reveals an ohmic electric response. The majority of the nanopores exhibit linear I-V curves and low 1/f noise upon fabrication in high salt (e.g., 1M KCl). Remaining nanopores that show signs of higher noise or self-gating can be conditioned, by applying moderate electric field pulses, to slightly enlarge them until ohmic behaviour is attained in high salt and neutral pHs. The I-V characteristics shown in FIG. 8 imply a relatively symmetric internal electric potential pore profile, which supports the symmetrical geometry with a uniform surface charge distribution assumed by the pore conductance model, also confirmed by TEM images.

The method described above may also be extended to fabricate rectifying nanopores with varying degree of rectification (i.e., behaving as diodes which pass current in one polarity but not the other). For example, small (<3 nm) nanopore fabricated in highly acidic solutions (e.g., 1M KCl pH 2) can rectify. If the pore is noisy, application of moderate AC electric field square pulses (e.g., low frequency pulses in the range of 0.2-0.3 V/nm for low-stress silicon nitride) to condition the pore should be done in an acidic solution as well. This preserves the rectification properties even as the pore is enlarged. The degree to which a pore rectifies can be increased by reducing the conductivity of the solution while maintaining the acidic pH, since the lower conductivity reduces screening and makes surface effects more important. Other techniques for achieving rectification are also contemplated.

Conversely, increasing the conductivity or moving toward neutral pH reduces rectification effects. Furthermore, the pore will conduct better in the bias opposite that in which it was created as long as the solution in the pore shares the same pH as that in which it was created. Reversing the solution from acidic to basic or vice versa has been demonstrated to reverse the direction of rectification. Given these observations, pore geometry and surface charge characteristics may be controlled by adjusting the pH of the solutions and the voltage polarity across the membrane.

To further characterize the nanopores, the noise in the ionic current is examined by performing power spectral density measurements. Remarkably, the fabrication method is able to consistently produce nanopores with low-1/f noise levels, comparable to fully wetted TEM-drilled nanopores. This may be attributed to the fact that nanopores are created directly in liquid rather than in vacuum, and are therefore never exposed to air. Thus far, hundreds of individual nanopores have been fabricated (e.g., ranging from 1 to 100-nm in size) with comparable electrical characteristics that are stable for days. Stability of the pores can be maintained by storing the pores in high salt concentration (e.g., >3M LiCl in water or in 1M LiCl in ethanol).

It is intriguing that the procedure described above triggers the fabrication of a single nanopore, particularly in a KCl aqueous solution, which is not known to chemically etch $SiN_x$ at neutral pH, and given that anodic oxidation of semiconductors or metals is known to produce arrays of nanopores. To elucidate the mechanisms leading to the formation of one pore in a dielectric membrane, the fabrication process is further investigated as a function of applied voltage, membrane thickness, electrolyte composition, concentration, and pH.

Figure 9A:
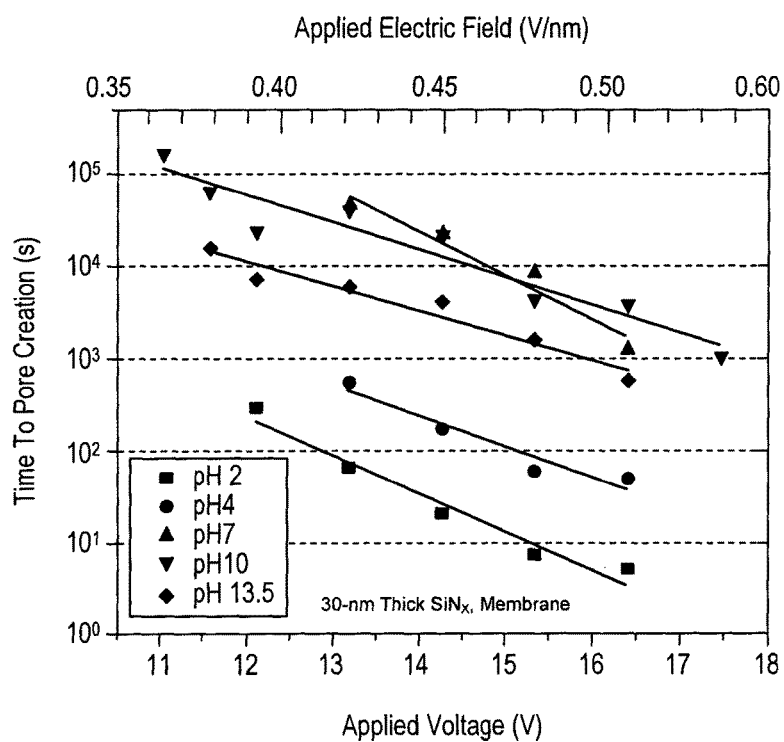
FIGS. 9A, 9B and 9C are graphs depicting time-to-pore creation as a function of trans-membrane potential for membranes having a 30 nm thickness, time-to-pore creation as a function of pH for membranes having a 30 nm thickness, and time-to-pore creation as a function of trans-membrane potential for membranes having a 10 nm thickness.
Figure 9B:
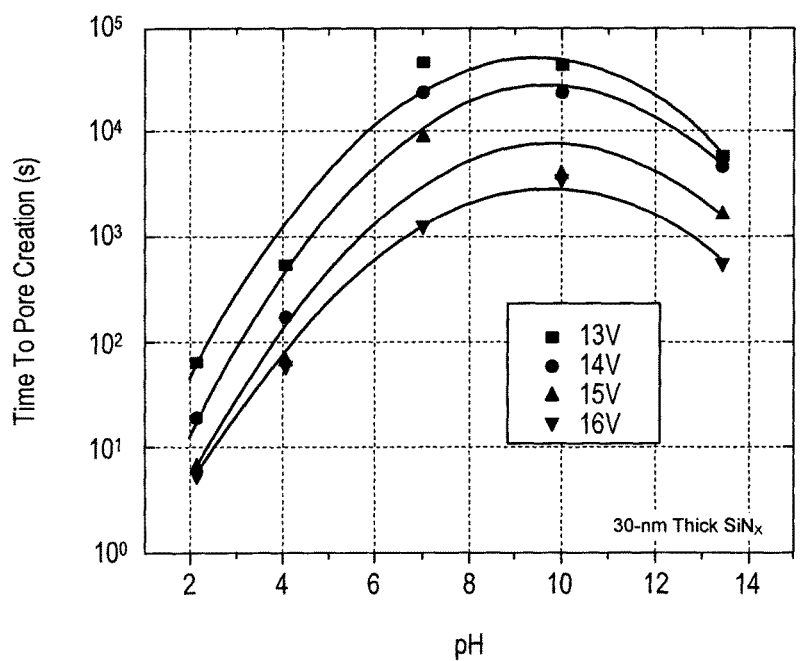

FIGS. 9A and 9B show the time-to-pore creation as a function of the trans-membrane potential for 30-nm-thick membranes, in 1M KCl buffered at various pHs. Interestingly, the fabrication time of a single nanopore scales exponentially with the applied voltage, and can be as short as a few seconds. For example, by increasing the voltage from 11 volts to 17 volts across a 30 nm thick $SiN_x$ membrane, the fabrication time can be reduced by 100 fold. By increasing the voltage from 4 volts to 10 volts on a 10 nm thick membrane, the fabrication time can be reduced by up to 1000 fold. Thus, increasing the applied electric potential reduces fabrication time. The same is true of the applied electric field.

The electrolyte composition also has a drastic effect on the fabrication time. In 1M KCl in water, fabrication time for a 30-nm thick $SiN_x$ membrane decreased 10-fold when going from pH7 to pH13.5 and decreased 1000-fold when going from pH7-pH2 for a given applied voltage. On a 10-nm thick $SiN_x$ membrane, the pH effect is less pronounced, with at most a 10-fold change. Asymmetric pH conditions between the two sides of the membrane also strongly affects the fabrication time depending on the voltage polarity (i.e. very fast fabrication times are obtained for: cathode/negative side at high pH and anode/positive side at low pH; and very slow fabrication times are obtained for cathode/negative side at low pH and anode/positive side at high pH).

Figure 9C:
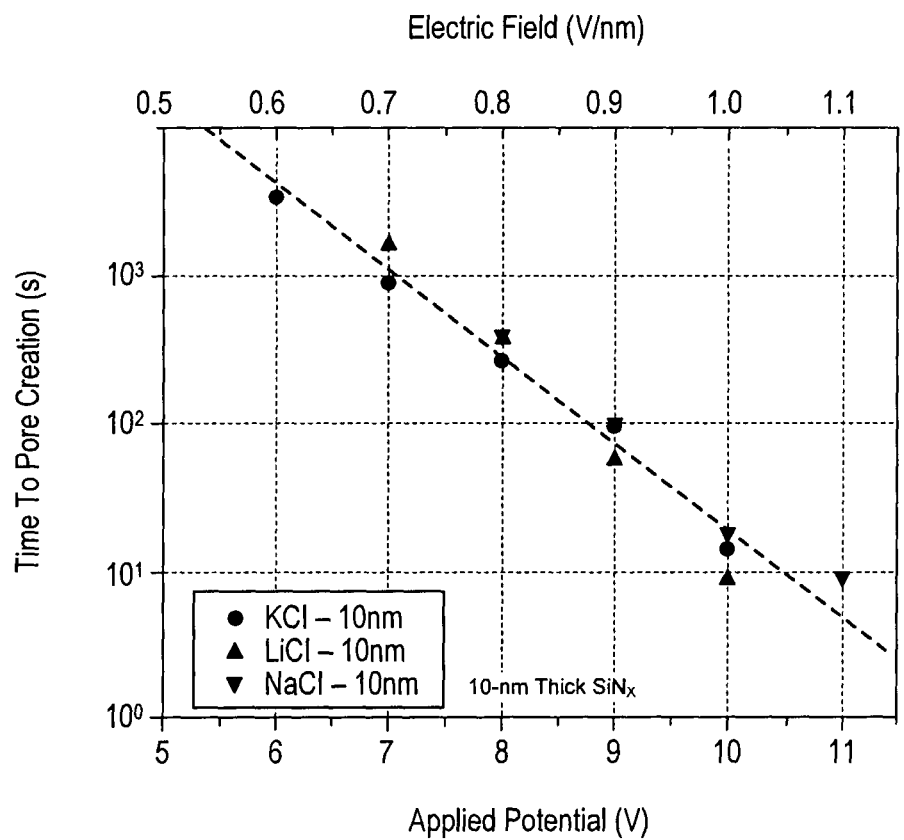

FIG. 9C shows the time-to-pore creation as a function of the trans-membrane potential for 10-nm-thick $SiN_x$ membranes, buffered at pH10 in various 1M Cl-based aqueous solutions. The fabrication time is again exponentially related to the trans-membrane potential, but the potential required for forming a nanopore is now reduced by ~⅓ as compared to 30-nm-thick membranes, irrespective of the different cationics ($K^+$, $Na^+$, $Li^+$) tested. Concentration levels of the electrolyte composition also had an effect on the fabrication time. For example, on a 30-nm thick $SiN_x$ membrane, fabrication time at low concentrations (~10 mM KCl in water) was significantly increased (i.e., >100-fold) as compared to high salt concentrations (1M and 3M KCl in water).

Nonetheless, these observations indicate that the applied electric field, $E=\Delta V/t$, across the membrane is the main driving force for initiating the fabrication of a single nanopore. Fields in the range of 0.4-1V/nm are close to the dielectric breakdown strength of low-stress $SiN_x$ films, and are key for intensifying the leakage current which is thought to ultimately cause breakdown in thin insulating layers. The exponential dependence of the time-to-pore creation on potential implies the same field dependency, which is reminiscent of the time-to-dielectric breakdown in gate dielectrics. Accordingly, dielectric breakdown mechanisms follow: (i) accumulation of charge traps (i.e. structural defects) by electric field-induced bond breakage or generated by charge injection from the anode or cathode, (ii) increasing up to a critical density forming a highly localized conductive path, and (iii) causing physical damage due to substantial power dissipation and the resultant heating. The process by which a single nanopore is fabricated in solution is similar, though the damage to the nanoscale is controlled by limiting the localized leakage current, at the onset of the first, discrete breakdown event. Ultimately a single nanopore is created since, for a fixed trans-membrane potential, the formation path of a nanopore experiences increased electric field strength during growth, which locally reinforces the rate of defect generation. The process by which material is removed from the membrane remains unclear, but broken bonds could be chemically dissolved by the electrolyte, or following a conversion to oxides or hydrides. The pH dependency on the fabrication time may be explained by the fact that breakdown at low pH is amplified by impact ionization producing an avalanche, due to the increased likelihood of holes injections, or $H^+$ incorporation, from the anode, which increases the rate of structural defect formation.

Figure 10:
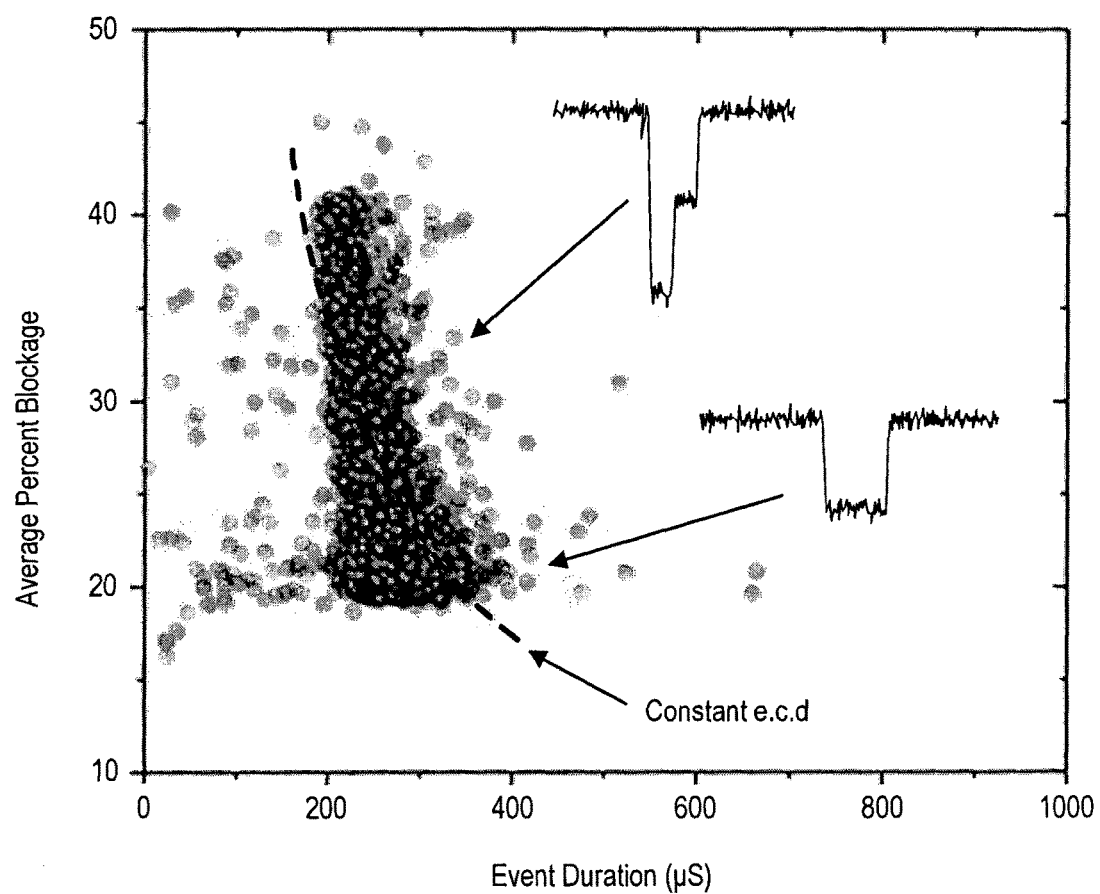
FIG. 10 is a scatter-plot of the normalized average current blockade versus the total translocation time of multiple single-molecule events.

DNA translocation experiments are performed to demonstrate that these nanopores can be leveraged for the benefit of single-molecule detection. Electrophoretically driven passage of a DNA molecule across a membrane is expected to transiently block the flow of ions in a manner that reflects the molecule length, size, charge and shape. The results using a 5-nm-diameter pore in a 10-nm-thick $SiN_x$ membrane are shown in FIG. 10. The scatter plot shows event duration and average current blockage of over 2,400 single-molecule translocations events of 5 kb dsDNA. The current drop is indicative of the molecule diameter (~2.2 nm) while the duration represents the time taken by a molecule to completely translocate through the pore. The characteristic shape of the events is indistinguishable to data obtained on TEM-drilled nanopores. The observed quantized current blockades strongly support the presence of a single nanopore spanning the membrane. Using dsDNA (~2.2 nm in diameter) as a molecular-sized ruler, the value of the single-level blockage events $\Delta G=7.4\pm0.4$ nS, provides an effective pore diameter consistent with size extracted from the pore conductance model.

Figure 11:
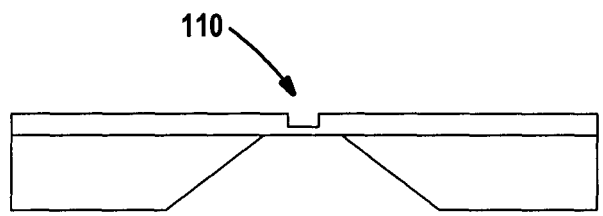
FIG. 11 is a diagram illustrating one technique for localizing formation of a nanopore.

Nanopore fabrication by controlled dielectric breakdown in solution represents a major step forward over current fabrication methods, and could provide an avenue towards commercialization of nanopore technology by enabling low-cost mass manufacturing of devices. While it is suspected that the nanopore creation process to be an intrinsic property of the dielectric membrane, such that the nanopore can form anywhere on the membrane surface, the current understanding strongly suggests that the position of the pore can be controlled by locally controlling the electric field strength or the material dielectric strength. For example, this could be achieved by locally thinning the membrane as indicated at 110 of FIG. 11. The electric field across the membrane can be estimated as $E=V/L$, where V is the applied voltage and L is membrane thickness. The threshold voltage for dielectric breakdown is therefore three times lower for the thinned region—ensuring that the nanopore is more likely to be created in this region, since fabrication time is exponentially related to field strength.

Figure 12:
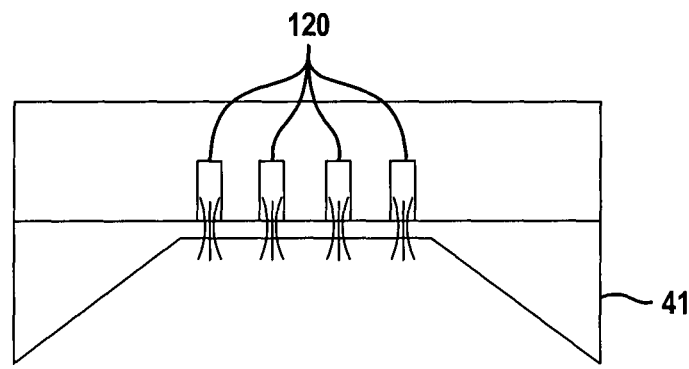
FIG. 12 is a diagram illustrating another technique for localizing formation of a nanopore.

In another example, the electric field can be confined to specific areas on the membrane, for example by using nano- or microfluidic channel encapsulation. With reference to FIG. 12, the nano- or microfluidic channels 120 are defined on the top side of the membrane 41. Each channel is independently addressable both fluidically and electrically. Four electrodes would be used on the top side; whereas, only one electrode is needed on the bottom side. A nanopore can be fabricated in each channel independently and when needed because the electric field is confined to the regions inside the channel. This approach would also allow for the simple integration of independently addressable nanopores in an array format on a single chip. It is envisioned that other techniques can be employed to focus the electric field in particular areas, such as placement of electrodes directly in contact with the surface of the membrane.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for fabricating a single nanopore in a membrane, comprising:
    selecting an electric potential that induces an electric field across an active area of the membrane, where the electric field has a value greater than 0.1 volt per nanometer across at least one point of the active area of the membrane prior to any removal of membrane material that would reduce thickness of the membrane in the active area;
    applying the electric potential across the membrane comprised of a dielectric material and thereby causing removal of membrane material;
    monitoring leakage current across the membrane while the electric potential is being applied across the membrane;
    detecting an abrupt increase in the leakage current across the membrane while the electric potential is being applied across the membrane; and
    removing the electric potential across the membrane in response to detecting the abrupt increase in the leakage current to stop the pore fabrication.

2. The method of claim 1 further comprises selecting an electric potential such that the electric field that approaches dielectric strength of the membrane material.

3. The method of claim 1 wherein detecting an abrupt increase in the leakage current further comprises determining a rate of change of the monitored current and comparing the rate of change to a threshold.

4. The method of claim 3 further comprises removing the electric potential when the rate of change of the monitored current exceeds the threshold, thereby stopping the fabrication.

5. The method of claim 1 wherein detecting an abrupt increase in the leakage current further comprises comparing a value of the monitoring current to a threshold and removing the electric potential when the value of the monitoring current exceeds a threshold, thereby stopping the fabrication.

6. The method of claim 1 further comprises
    disposing the membrane between two reservoirs filled with a fluid containing ions, such that the membrane separates the two reservoirs and prevents the fluid from passing between the two reservoirs;
    placing an electrode into each of the two reservoirs; and
    generating the electric potential using the electrodes.

7. The method of claim 6 further comprises placing one of the two electrodes into direct contact with the membrane.

8. The method of claim 1 further comprises increasing the applied electric potential to reduce fabrication time.

9. The method of claim 1 further comprises increasing the electric field in the membrane to reduce fabrication time.

10. The method of claim 6 further comprises increasing concentration of ions in the fluid to reduce fabrication time.

11. The method of claim 6 further comprises increasing acidity of the fluid to reduce fabrication time.

12. The method of claim 6 further comprises increasing alkalinity of the fluid to reduce fabrication time.

13. The method of claim 6 further comprises changing acidity of the fluid in one reservoir in relation to the fluid in the other reservoir to change fabrication time.

14. The method of claim 6 further comprises adjusting acidity of the fluid on each side of the membrane to control geometry and surface charge characteristic of the pore.

15. The method of claim 6 further comprises adjusting polarity of the electric potential in the membrane to control geometry and surface charge characteristic of the pore.

16. The method of claim 1 wherein the nanopore is formed in the active area of the membrane.

17. A method for fabricating a single nanopore in a membrane, comprising:
    selecting an electric potential that induces an electric field across an active area of the membrane, where the electric field has a value greater than 0.1 volt per nanometer across thickest part of the active area of the membrane prior to any removal of membrane material caused by the electric potential;
    applying the electric potential across the membrane comprised of a dielectric material and thereby causing removal of membrane material;
    monitoring leakage current across the membrane while the electric potential is being applied across the membrane;
    detecting an abrupt increase in the leakage current across the membrane while the electric potential is being applied across the membrane; and
    removing the electric potential across the membrane in response to detecting the abrupt increase in the leakage current to stop the pore fabrication.

18. A method for fabricating a single nanopore in a membrane, comprising:
    selecting an electric potential that induces an electric field across an active area of the membrane, where the electric potential has a value greater than one volt and the electric field has a value greater than 0.1 volt per nanometer across the active are of the membrane;
    applying the electric potential across the membrane comprised of a dielectric material and thereby causing removal of membrane material;
    monitoring leakage current across the membrane while the electric potential is being applied across the membrane;
    detecting an abrupt increase in the leakage current across the membrane while the electric potential is being applied across the membrane; and
    removing the electric potential across the membrane in response to detecting the abrupt increase in the leakage current to stop the pore fabrication.

* * * * *